US007844329B2

(12) United States Patent
Chambers

(10) Patent No.: US 7,844,329 B2
(45) Date of Patent: Nov. 30, 2010

(54) IMPLANTABLE ELECTRICAL CONNECTOR

(75) Inventor: John Chambers, Mona Vale (AU)

(73) Assignee: Cochlear Limited, Lane Cove (AU)

( * ) Notice: Subject to any disclaimer, the term of this patent is extended or adjusted under 35 U.S.C. 154(b) by 0 days.

(21) Appl. No.: 12/035,940

(22) Filed: Feb. 22, 2008

(65) Prior Publication Data
US 2009/0215296 A1 Aug. 27, 2009

(51) Int. Cl.
A61N 1/00 (2006.01)
(52) U.S. Cl. ........................................................ 607/2
(58) Field of Classification Search ............... 607/5, 607/37, 2; 73/52; 600/392; 439/587, 312, 439/102
See application file for complete search history.

(56) References Cited
U.S. PATENT DOCUMENTS

| | | | | | |
|---|---|---|---|---|---|
| 3,941,444 | A | * | 3/1976 | Bruni et al. | 439/587 |
| 4,017,139 | A | * | 4/1977 | Nelson | 439/352 |
| 4,126,126 | A | * | 11/1978 | Bare et al. | 600/392 |
| 4,179,180 | A | * | 12/1979 | Hanna | 439/102 |
| 6,129,747 | A | * | 10/2000 | Lindegren | 607/37 |
| 7,299,095 | B1 | * | 11/2007 | Barlow et al. | 607/37 |
| 7,316,154 | B1 | * | 1/2008 | Bennett | 73/52 |
| 2005/0038476 | A1 | * | 2/2005 | Brown | 607/5 |

* cited by examiner

Primary Examiner—George Manuel
Assistant Examiner—Robert N Wieland
(74) Attorney, Agent, or Firm—Kilpatrick Stockton LLP

(57) ABSTRACT

An implantable connector for connecting components of implantable medical devices. The connector comprises first and second connector halves electrically coupled to the implantable components. A sealing membrane is provided to seal the electrical connection between the first and second connector halves. The sealing membrane is configured to be ruptured with a minimal amount of force so that the connector halves may be readily disconnected from each other.

49 Claims, 10 Drawing Sheets

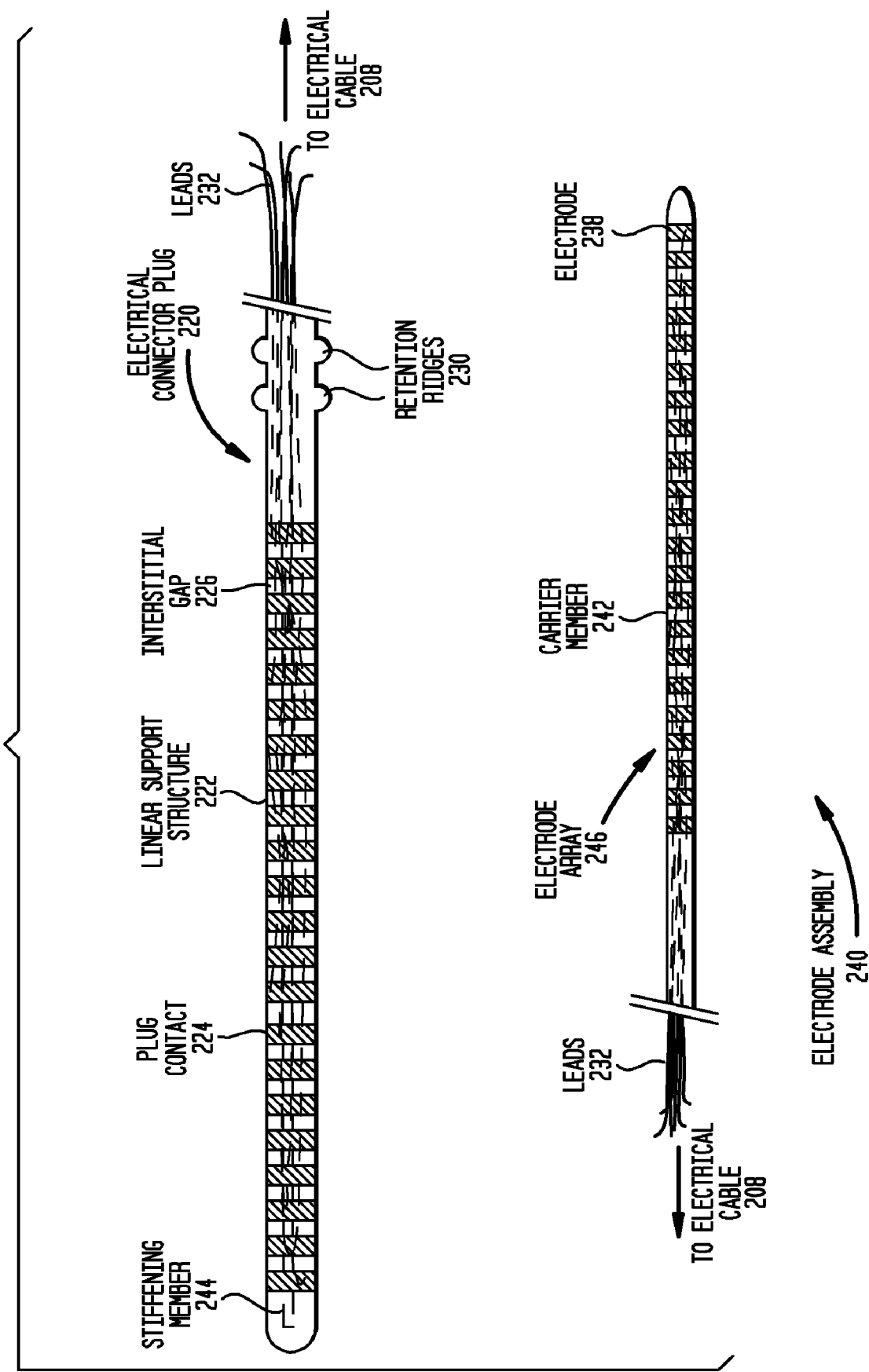

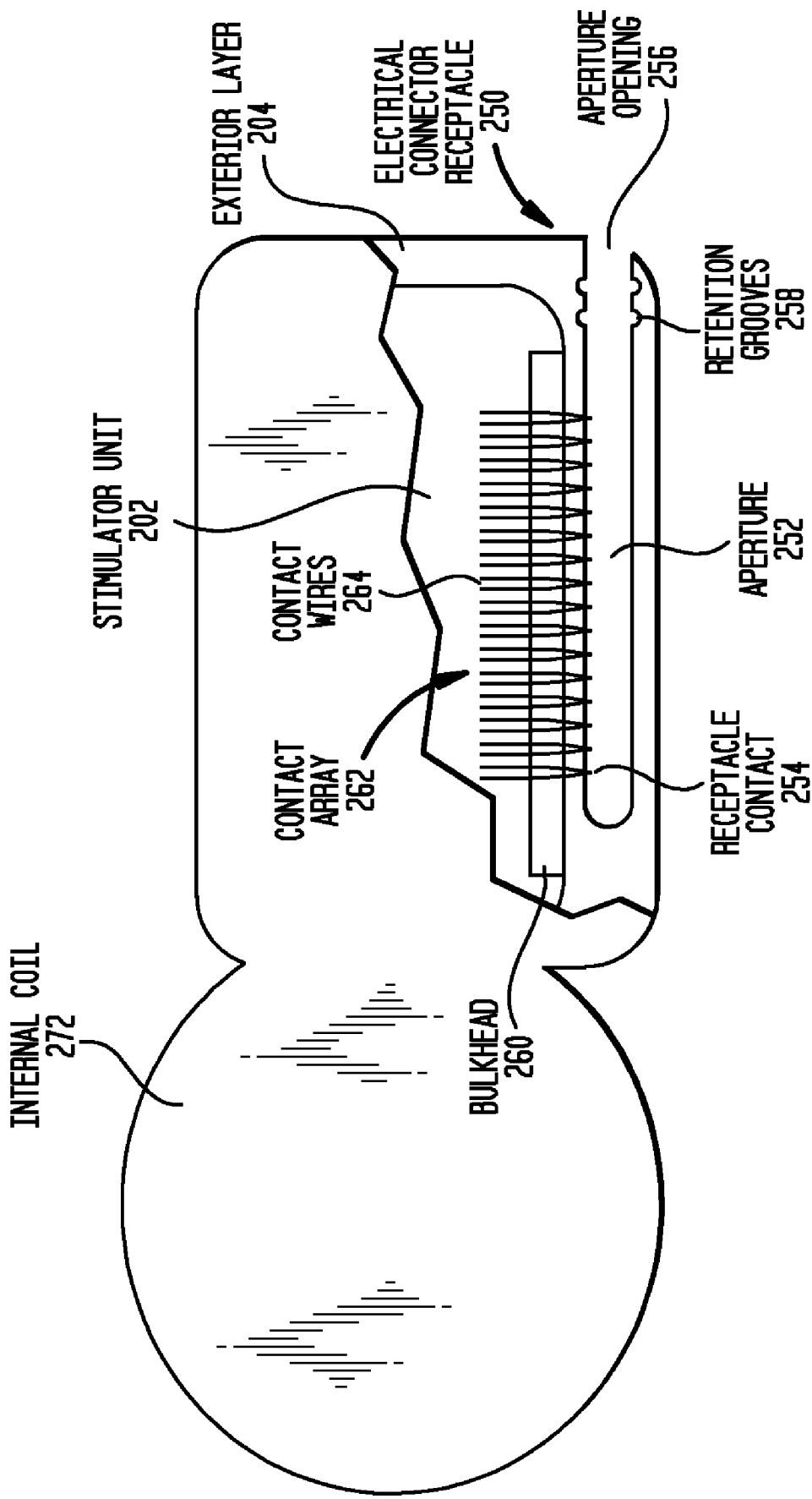

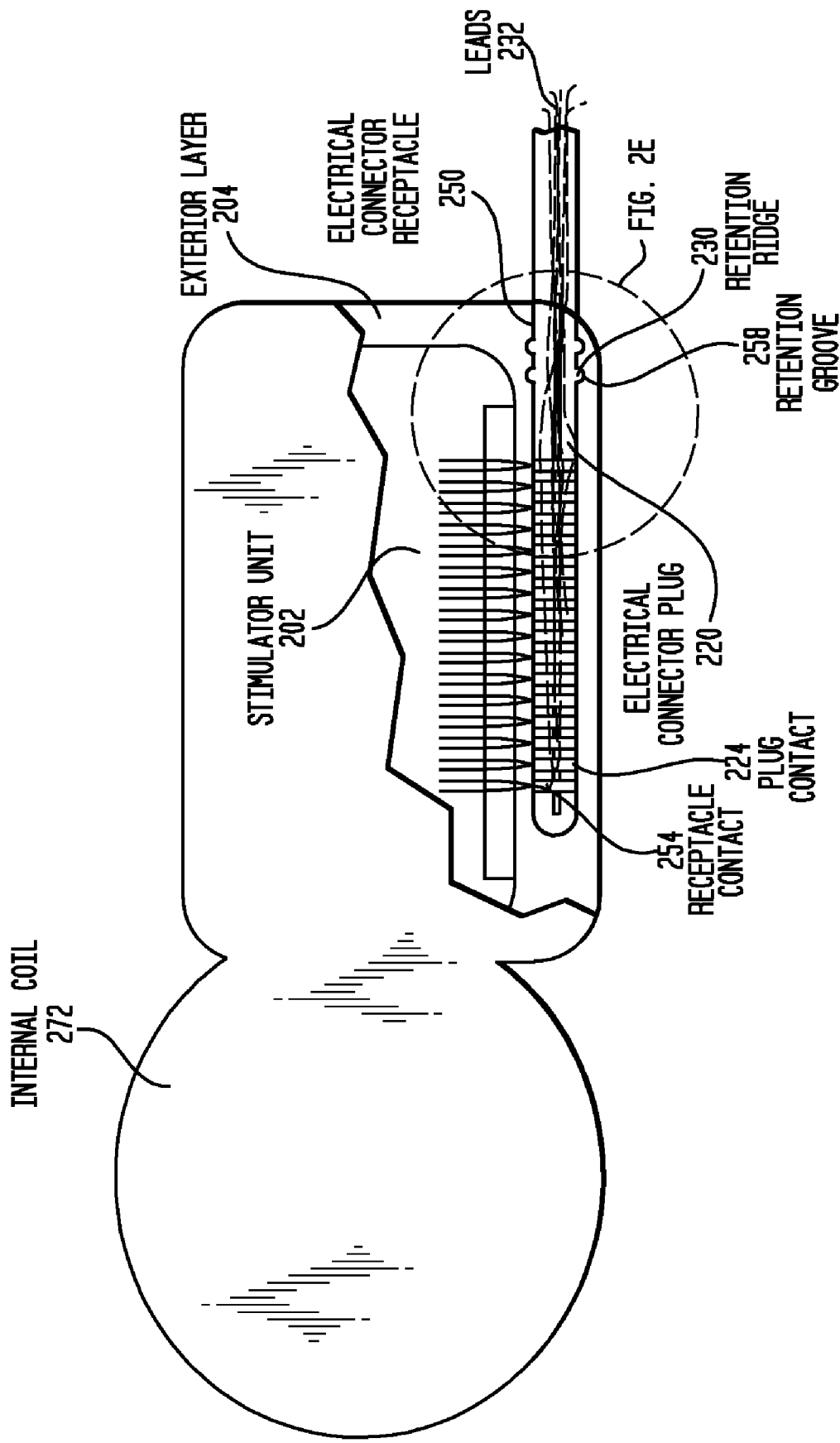

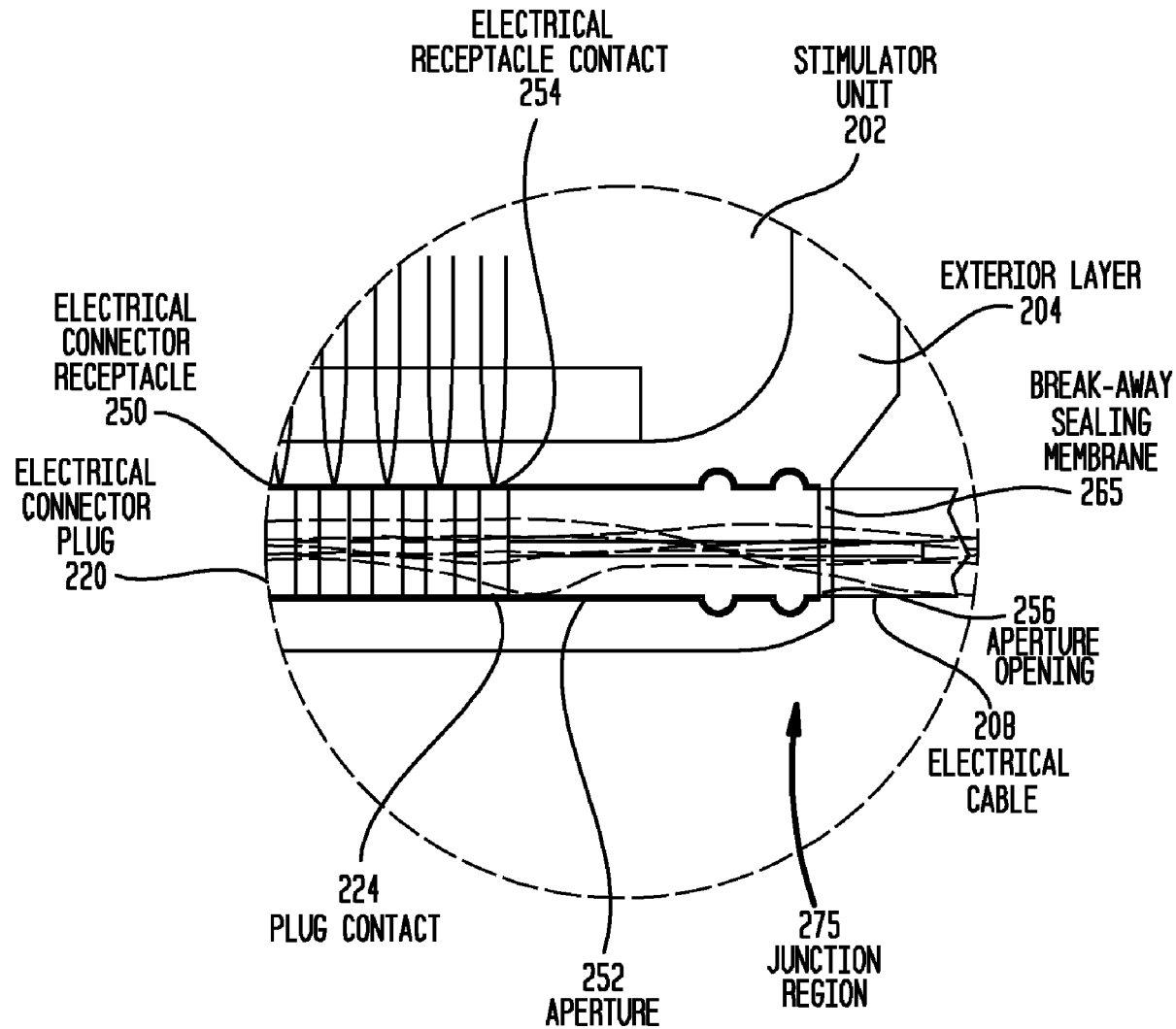

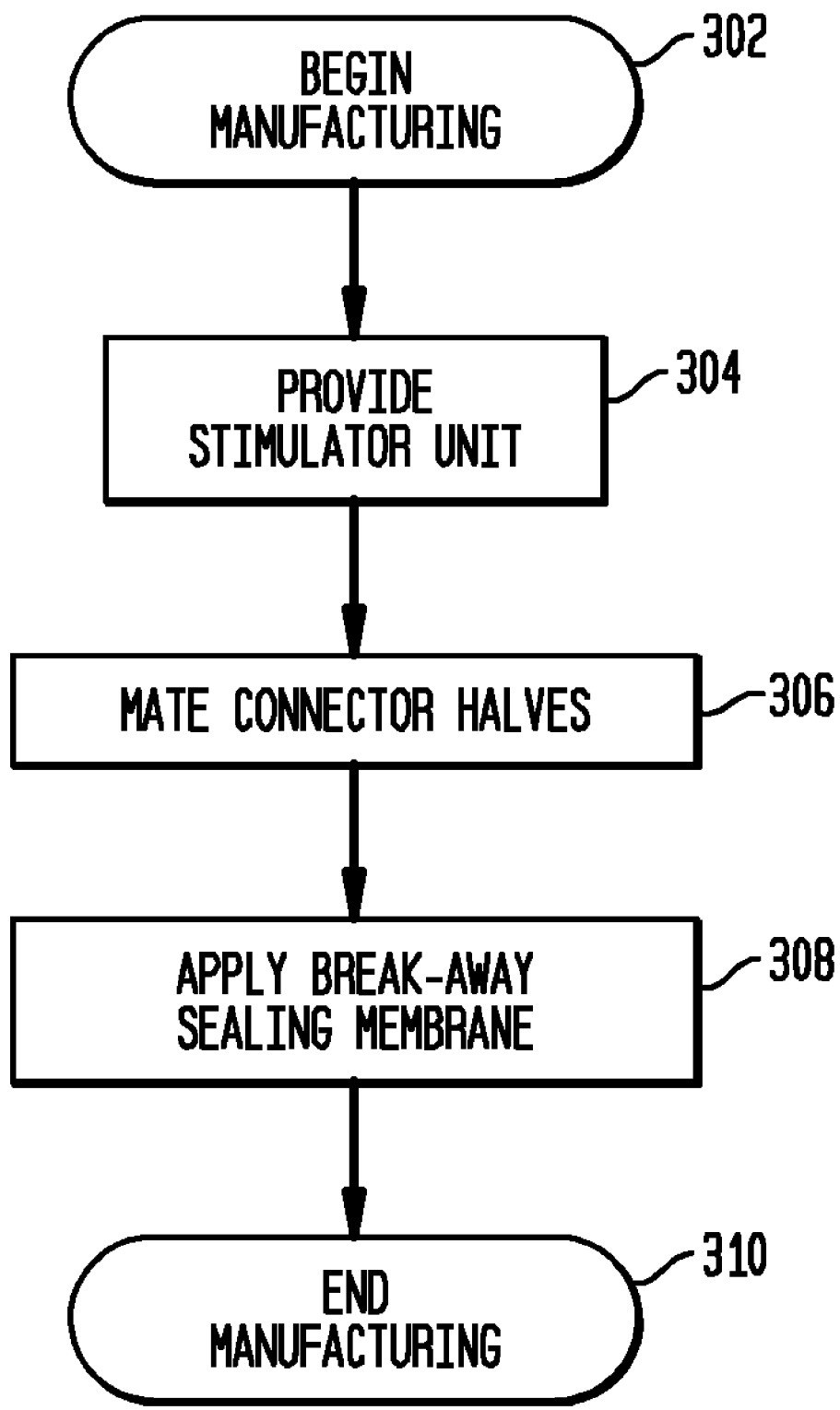

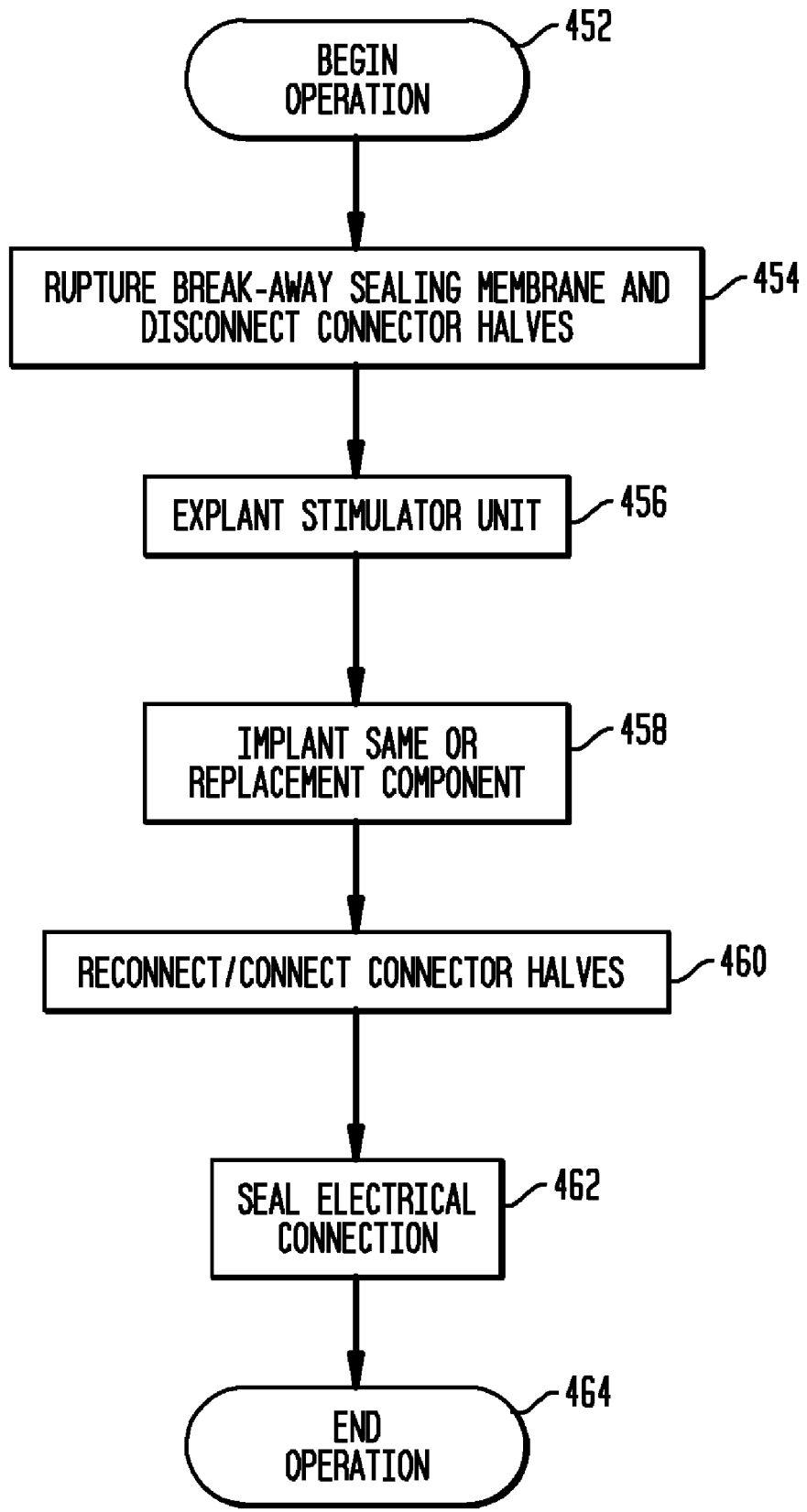

IMPLANTABLE ELECTRICAL CONNECTOR

BACKGROUND

1. Field of the Invention

The present invention relates generally to implantable medical devices, and more particularly, to an implantable electrical connector.

2. Related Art

Medical devices having one or more implantable components, generally referred to as implantable medical devices, have provided a wide range of therapeutic benefits to patients over recent decades. One type of implantable medical device that has provided substantial benefits to patients is the prosthetic hearing device. Prosthetic hearing devices process ambient sound to supplement or provide hearing ability to a hearing impaired patient.

Prosthetic hearing devices include a category of implantable devices known as Cochlear™ implants (also referred to as Cochlear™ devices, Cochlear™ implant devices, and the like; "cochlear implants" herein). (COCHLEAR is a trademark of Cochlear Limited, Lane Cove, NSW, Australia.) Cochlear implants include one or more microphones to receive ambient sound and a speech processor. The speech processor may be worn by, or implanted in, the recipient. The speech processor processes ambient sound received by one or more microphones, typically located in a behind-the-ear housing worn on the recipient's auricle.

Cochlear implants also include an array of stimulation electrodes disposed on the distal end of an elongate electrode assembly which is implanted in the cochlea of the patient (sometimes referred to herein as a recipient). The electrode array is controlled by an electronic system encased in a hermetically sealed, biocompatible housing which is typically implanted in the mastoid. The electronic system, commonly referred to as a stimulator unit, essentially contains decoder and driver circuits for the stimulation electrodes.

In current cochlear implants, the stimulator unit may require replacement or adjustment for various reasons, such as device failure, infection, replacement or replenishment of batteries or other energy storage systems, etc. However, in current cochlear implants, one or more wires directly connect electrodes of the electrode array with the stimulator unit. These direct wiring arrangements make the removal and re-attachment of the stimulator unit impracticable without disturbing the position of the electrode assembly. Such arrangements are problematic because disturbance of the electrode assembly may result in damage to the delicate structures of the cochlea or other body tissue.

SUMMARY

In one aspect of the present invention, a medical device is disclosed. The medical device comprises: first and second implantable components; an electrical connector configured to electrically connect the first and second components, comprising: first and second connector halves electrically coupled to the first and second components, respectively, and a sealing membrane configured to seal the electrical connection between the first and second connector halves, wherein the sealing membrane is configured to be ruptured with a minimal amount of force so that the first and second connector halves may be readily disconnected from each other.

In another aspect of the present invention, a method of reconfiguring an first implanted component electrically connected to a second implanted component via an electrical connector, the electrical connector comprising first and second connector halves electrically coupled to the first and second components, respectively, and a sealing membrane configured to seal the electrical connection between the first and second connector halves. The method comprises: opening the site of the implanted components; rupturing the sealing membrane with the application of minimal force; separating the connector halves so as to electrically disconnect the first and second components; and adjusting the configuration of the first component.

In a third aspect of the present invention a method of manufacturing a medical device is disclosed. The method comprises: providing a first implantable component electrically coupled to a first connector half; providing a second implantable component electrically coupled to a second connector half; mating the first and second connector halves so as to electrically connect the first and second components; and sealing the electrical connection between the first and second mated halves with a sealing membrane, wherein the sealing membrane is configured to be ruptured upon the application of a minimal so that the first and second connector halves may be disconnected from each other.

In a fourth aspect of the present invention a connector for electrical connector that electrically connects implantable components is disclosed. The connector comprises: first and second connector halves electrically coupled to first and second components, respectively; and a sealing membrane configured to seal the electrical connection between the first and second connector halves, wherein the sealing membrane is configured to be ruptured with a minimal amount of force so that the first and second connector halves may be readily disconnected from each other.

BRIEF DESCRIPTION OF THE DRAWINGS

Illustrative embodiments of the present invention are described herein with reference to the accompanying drawings, in which:

FIG. 2B is a perspective view of the electrode assembly depicted in FIG. 2A broken away to illustrate an embodiment of the electrical connector plug of the electrical connector illustrated in FIG. 2A;

FIG. 2C is a perspective view of the stimulator unit depicted in FIG. 2A broken away to illustrate an embodiment of the electrical connector receptacle of the electrical connector illustrated in FIG. 2A;

FIG. 2D is a perspective view of the stimulator unit illustrated in FIG. 2A broken away to illustrate the mated arrangement of the electrical connector plug of FIG. 2B and the electrical connector receptacle of FIG. 2C, in accordance with embodiments of the present invention;

FIG. 2E is an enlarged view of a portion of the mated arrangement of the electrical connector plug and the electrical connector receptacle of FIG. 2D;

FIG. 3 is a flowchart illustrating the manufacture of embodiments of a stimulator unit and an electrode assembly in accordance with embodiments of the present invention;

FIG. 4 is a flowchart illustrating the replacement of a stimulator unit, in accordance with embodiments of the present invention;

DETAILED DESCRIPTION

Figure 1:
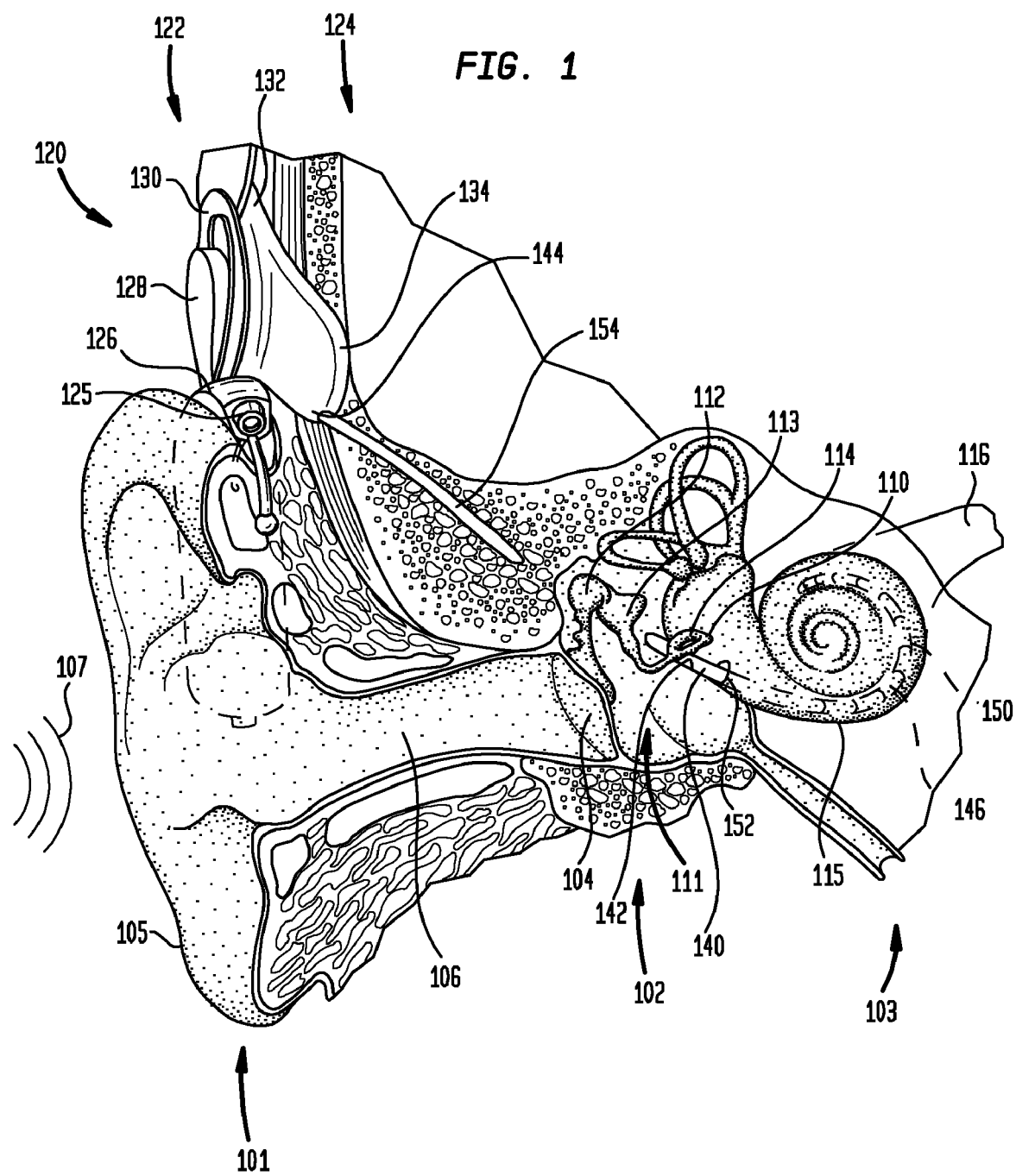
FIG. 1 is a perspective view of an exemplary implantable medical device, a cochlear implant, in which embodiments of the present invention may be advantageously implemented.

Aspects of the present invention are generally directed to an electrical connector that electrically connects two implantable components of an implantable medical device. The electrical connector comprises two mating halves each electrically coupled to one of the implantable components. The electrical connector is sealed to maintain the integrity of the electrical connection while the connector halves are connected ("mated" herein regardless of connector configuration). The seal is provided by a membrane that protects at least the electrical connections of the mated connector halves. The sealing membrane is configured to be ruptured so as to allow the implanted components to be disconnected from each other with minimal force. In one embodiment, the membrane is configured to rupture when subjected to a force having a magnitude that is approximately the same as the magnitude of the force which is necessary to manually disconnect the connector halves without the presence of the sealing membrane. In one specific embodiment, the membrane is configured to rupture when subjected to a manual force applied by a surgeon to manually disconnect the connector halves.

In embodiments of the present invention, one or both of the components are physically connected to the respective connector halves, for example, to provide a direct electrical there between. In certain applications of the present invention, one or both of the components are electrically coupled to the respective connector halves via a cable or other flexible element. Such a flexible element is configured to allow a connector half to be moved within the patient adjacent to the surgical space without causing movement of its associated component. This permits the physical separation of the components without causing translation, rotation or otherwise physically disturbing one or both components. In some embodiments, the ability to disconnect the components without disturbing one or both components permits the independent explantation of a component from the recipient while leaving the other component in a stationary implanted position. In such embodiments, subsequent connection of a repaired or replacement component may be attained by mating the connector halves and reestablishing the seal.

Exemplary embodiments of the present invention are described herein with reference to one type of implantable medical device, a prosthetic hearing device, namely, a cochlear implant. It should be appreciated that an electrical connector in accordance with embodiments of the present invention may be used in alternative implantable devices, and may be used to connect a variety of components. For example, in one application, the electrical connector of the present invention may be used to connect an auxiliary power source to an implanted component. The following discussion has been provided for illustration purposes and should not be construed as limiting the present invention.

The exemplary cochlear implant described below comprises two implantable components, a stimulator unit and an electrode assembly, electrically connected with an embodiment of the electrical connector of the present invention. As will be described in detail below, the electrical connector is configured to maintain the integrity of the electrical connection between the electrode assembly and the stimulator unit and to permit disconnection of the components. In certain embodiments, the stimulator may be electrically connected to, or disconnected from, the electrode assembly without physically disturbing the implanted electrode assembly, thereby permitting removal of the stimulator unit without risking damage to the fine structures of the cochlea that commonly attend the implantation and explantation of electrode assemblies.

FIG. 1 illustrates an exemplary cochlear implant in which aspects of the present invention may be implemented. In a fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 115. Such fluid motion, in turn, activates tiny hair cells (not shown) that line the inside of cochlea 115. Activation of the hair cells causes appropriate nerve impulses to be transferred through the spiral ganglion cells and auditory nerve 116 to the brain (not shown), where they are perceived as sound. In certain profoundly deaf persons, there is an absence or destruction of the hair cells. Cochlear implants, such a cochlear implant 120, are utilized to directly stimulate the ganglion cells to provide a hearing sensation to the recipient.

FIG. 1 also illustrates the positioning of cochlear implant 120 relative to outer ear 101, middle ear 102 and inner ear 103. Cochlear implant 120 comprises external component assembly 122 which is directly or indirectly attached to the body of the recipient, and an internal component assembly 124 which is temporarily or permanently implanted in the recipient. External assembly 122 comprises microphone 125 for detecting sound which is output to a behind-the-ear (BTE) speech processing unit 126 that generates coded signals which are provided to an external transmitter unit 128, along with power from a power source 129 such as a battery. External transmitter unit 128 comprises an external coil 130 and, preferably, a magnet (not shown) secured directly or indirectly in external coil 130.

Alternative embodiments of cochlear implants may also use a totally implantable arrangement. In such embodiments, the speech processor and/or the microphone may be implanted in the recipient. Such totally implantable devices are described in, for example, by H. P. Zenner et al. "First implantations of a totally implantable electronic hearing system for sensorineural hearing loss", in HNO Vol. 46, 1998, pp. 844-852; H. Leysieffer et al. "A totally implantable hearing device for the treatment of sensorineural hearing loss: TICA LZ 3001", in HNO Vol. 46, 1998, pp. 853-863; and H. P. Zenner et al. "Totally implantable hearing device for sensorineural hearing loss", in The Lancet Vol. 352, No. 9142, page 1751, the contents of which are hereby incorporated by reference herein.

In the cochlear implant embodiment illustrated in FIG. 1, internal component assembly 124 comprise an internal coil 132 of a stimulator unit 134 that receives and transmits power and coded signals received from external assembly 122 to other elements of stimulator unit 134 which apply the coded signal to cochlea 115 via an implanted electrode assembly 140. Connected to stimulator unit 134 is a flexible cable 154. Flexible cable 154 electrically couples stimulator unit 134 to electrode assembly 140. Electrode assembly 140 comprises a carrier member 142 having one or more electrodes 150 positioned on an electrode array 146. Electrode assembly 140 enters cochlea 115 at cochleostomy region 152 and is positioned such that electrodes 150 are substantially aligned with portions of tonotopically-mapped cochlea 115. Signals generated by stimulator unit 134 are typically applied by the array 146 of electrodes 150 to cochlea 115, thereby stimulating auditory nerve 116.

Given the coiled shape of cochlea 115, carrier member 142 is typically constructed using a material, or combination of materials, which curls or is capable of being curled in a manner which follows the curvature of cochlea 115. The portion of electrode assembly 140 intended to be inserted into cochlea 115 will often have a stiffening stylet (not shown) inserted into a channel, for example a lumen (not shown), which extends distally from the proximate end of electrode carrier member 142. During implantation of electrode assembly 140, the stylet contained in the lumen of carrier member 142 is removed from the proximate end of the carrier member as the carrier member is inserted into cochlea 115. The act of removing the stiffening stylet from the lumen allows electrode carrier member 142 to curl. In further embodiments of cochlear implant 120, the stiffness of the stylet decreases in response to fluids and/or body temperature allowing electrode carrier member 142 to curl in order to follow the curvature of the inner walls of cochlea 115. In other embodiments of cochlear implants, electrode carrier member 142 is naturally straight without the assistance of a stylet inserted into the lumen. Such embodiments of electrode carrier member 142 are constructed using a flexible material, or is constructed so as to flex upon a fixed amount of force being exerted on the tip or body of electrode carrier member 142 as it is being inserted into cochlea 115. If further embodiments of cochlear implants, a stylet may be inserted into the lumen of electrode carrier member 142, where the stylet interact with fluids and/or some level of body temperature such that the stiffness of the stylet breaks in order to allow the carrier member to curl in order to follow the curvature of the inner walls of cochlea 115.

Although the present invention will discussed herein with reference to a cochlear implant it should be appreciated that the present invention may be implemented in a variety of implantable devices. For example, such devices in which embodiments of the present invention may include, but are limited to, implantable neural stimulators, pacemakers, implantable pumps, etc.

Figure 2A:
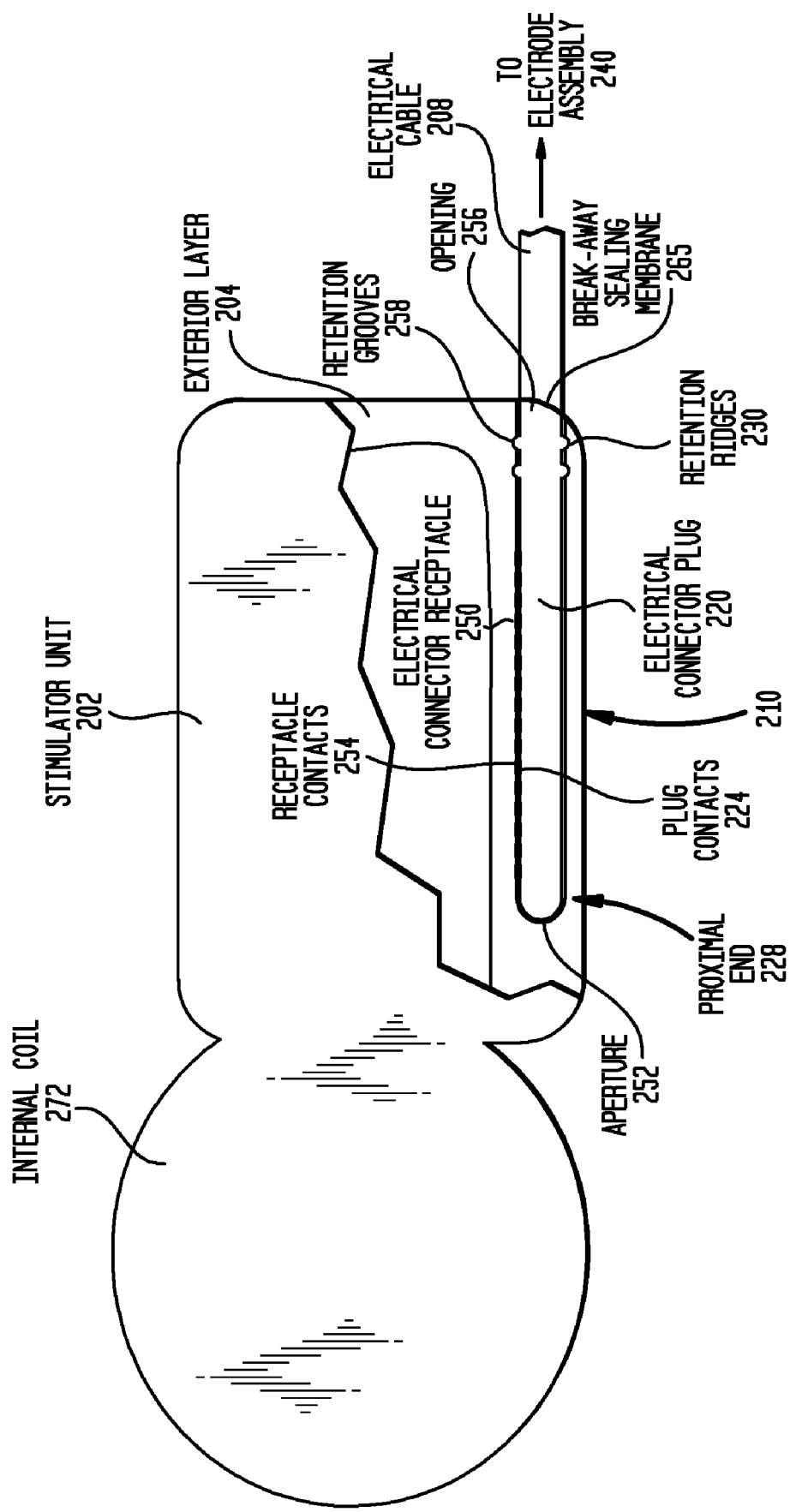
FIG. 2A is a perspective of the stimulator unit depicted in FIG. 1 partially broken away to illustrate the electrical connection of the stimulator unit and the electrode assembly of FIG. 1 via an embodiment of the electrical connector of the present invention.

An electrical connector in accordance with aspects of the present invention is described below with reference to FIGS. 2A-2E. FIG. 2A is a perspective view of a stimulator unit 202 electrically connected to an electrode assembly 240 (not shown) via an electrical connector 210. In the embodiment shown in FIG. 2A, stimulator unit 202 is an embodiment of stimulator 134 of FIG. 1 and is configured to generate and transmit stimulation signals to electrode assembly 240. Internal coil 272 is similar to internal coil 172 of FIG. 1 and is configured to receive and transmit power and coded signals received from an external assembly to other elements of stimulator unit 202. Electrode assembly 240 comprises an embodiment of electrode assembly 140 of FIG. 1 and is configured to deliver stimulation to the cochlea of the recipient.

In the embodiment of FIG. 2A, electrical connector 210 comprises two connector halves. A first connector half is electrically coupled to stimulator unit 202 and comprises an electrical connector receptacle 250. A second connector half is electrically coupled to electrode assembly 240 and comprises an electrical connector plug 220. Electrical connector plug 220 is mated with electrical connector receptacle 250 by inserting connector plug 220 into electrical connector receptacle 250.

Electrical connector 210 is sealed to maintain the integrity of the electrical connection between electrical connector receptacle 250 and electrical connector plug 220 while the connector halves are mated. The seal is provided by a break-away sealing membrane 265 that protects at least the electrical connections between electrical connector receptacle 250 and electrical connector plug 220. Break-away sealing membrane may comprise an ingress barrier configured to substantially prevent the ingress of fluids there through. Break-away sealing membrane 265 is configured to be ruptured so as to allow stimulator unit 202 and electrode assembly 240 to be disconnected from each other with minimal force. In one embodiment, break-away sealing membrane 265 is configured to rupture when subjected to a force having a magnitude that is approximately the same as the magnitude of the force which is necessary to manually disconnect electrical connector plug 220 from electrical connector receptacle 250 without the presence of the break-away sealing membrane 265. In one specific embodiment, sealing membrane 265 is configured to rupture when subjected to a manual force applied by a surgeon to manually disconnect electrical connector plug 220 from electrical connector receptacle 250 from one another.

In certain applications of the present invention, one or both of electrode assembly 240 and stimulator unit 202 are electrically coupled to their respective connector halves, electrical connector plug 220 and electrical connector receptacle 250, via a flexible element or cable. Such a flexible element is configured to allow electrical connector plug 220 or electrical connector receptacle 250 to be moved within the patient adjacent to, or within, the surgical space without causing movement of its associated component, electrode assembly 240 or stimulator unit 202, respectfully. This permits the physical separation of electrode assembly 240 and stimulator unit 202 without causing translation, rotation or otherwise physically disturbing one electrode assembly 240. In some embodiments, the ability to disconnect stimulator unit 202 without disturbing electrode assembly 240 permits the independent explantation of stimulator unit 202 from the recipient while leaving electrode assembly 240 implanted in the cochlea of the recipient. In such embodiments, subsequent connection of a repaired or replacement stimulator unit 202 may be attained by mating electrical connector plug 220 with electrical connector receptacle 250 and reestablishing break-away sealing membrane 265.

Break-away sealing membrane 265 may comprise silicone, parylene, silicone elastomer, or other biocompatible material that is substantially resistant to the ingress of biological fluids making it suitable or appropriate for providing a seal. In certain embodiments, break-away sealing membrane 265 may be applied via a coating process. In alternative embodiments, the application of break-away sealing membrane 265 may take other forms. For example, in one embodiment, the application of sealing membrane 265 comprises dipping the mated connector halves into a tank of liquid biocompatible material. In other embodiments, the coating process comprises spraying the biocompatible material about electrical connector 210. In still other embodiments, the coating process may comprise the manual application of an epoxy or other surface sealant. It should be appreciated that any other process for applying a material may also be used to apply break-away sealing membrane 265.

In the embodiment illustrated in FIG. 2A, an exterior layer 204 is provided on the surface of stimulator 202. For ease of illustration, exterior layer 204 has been shown partially removed in FIG. 2A. Similar to break-away sealing membrane 265, exterior layer 204 may comprise a biocompatible material configured to seal stimulator unit 202, and may comprise silicone, parylene, silicone elastomer, or other biocompatible material. Exterior layer 204 may be applied via any of the coating processes described above with reference to the application of break-away sealing membrane 265. In certain embodiments, exterior layer 204 may comprise a hermetic sealing layer.

As described below with reference to FIG. 2C, in certain embodiments, electrical connector receptacle 250 is integrated within exterior layer 204. In these embodiments, electrical connector receptacle 250 is electrically coupled to stimulator unit 202 via wires extending through exterior layer 204. However, as is discussed below in more detail, electrical connector receptacle 250 may be electrically coupled to stimulator unit 202 in a variety of manners, including via a flexible cable.

In the embodiment illustrated in FIG. 2A, flexible electrical cable 208 is provided to electrically couple electrical connector plug 220 to electrode assembly 240. As noted above, flexible cable 208 assists in the physical separation of stimulator unit 202 from electrode assembly 240 without causing translation, rotation or otherwise physically disturbing electrode assembly 240 implanted in the cochlea of the recipient. In such embodiments, following the rupture of break-away sealing membrane 265, electrical connector plug 220 may be moved or repositioned with disturbing the position of electrode assembly 240.

FIG. 2B is a perspective view of electrical connector plug 220 of FIG. 2A broken away from electrode assembly 240. Electrical connector plug 220 and electrode assembly 240 have been shown separated for ease of illustration, but it should be appreciated that electrical connector plug 220 and electrode assembly 240 are connected via electrical cable 208.

As described above with reference to FIG. 1, electrode assembly 240 comprises a flexible carrier member 242 having an array 246 of electrodes 238 to deliver stimulation to the cochlea of the recipient. Also, as described above with reference to carrier member 142 of FIG. 1, carrier member 242 may comprise a resiliently flexible material or combination of materials, which curl or are capable of being curled in a manner which follows the curvature of the recipient's cochlea 115.

In the embodiment illustrated in FIG. 2B, electrical connector plug 220 comprises a support structure 222 of resiliently flexible material or combination of materials. In the illustrative embodiment of FIG. 2B, support structure 222 comprises a substantially straight elongate member, referred to as linear support structure 222. Disposed in or on linear support structure 222 is a plurality of plug contacts 224 separated by interstitial gaps 226. As described below with reference to FIG. 2D, plug contacts 224 are configured to be electrically coupled to elements of electrical connector receptacle 250. Interstitial gaps 226 comprise insulating portions of linear support structure 222 that electrically insulate plug contacts 224 from one another.

Further illustrated in FIG. 2B are leads 232. Leads 232 extend from one or more electrodes 238 through electrical cable 208 to one or more plug contacts 224. In the embodiments shown in FIG. 2B, a single lead 232 extends between a plug contact 224 and an electrode 238. However, it should be appreciated that in alternative embodiments of the present invention, a lead 232 may extend between any number of plug contacts 224 or electrodes 238. For example, a lead 232 may extend from one plug contact 224 to a plurality of electrodes 238. Likewise, in alternative embodiments, a lead 232 may extend from a plurality of plug contacts 224 to a single electrode 238.

In some embodiments of the present invention, an electrical cable 208 connects electrical connector plug 220 to electrode assembly 240. In these embodiments, electrical cable 208 comprises a flexible material having one or more lumens there through. Leads 232 extend through the one or more lumens of electrical cable 208. In certain embodiments, electrical cable 208 may comprise a resiliently flexible material or combination of materials configured to adopt a desired or predetermined configuration.

As noted above, in the embodiments illustrated in FIGS. 2A-2E, electrical connector plug 220 is inserted into electrical connector receptacle 250 to electrically connect stimulator unit 202 to electrode assembly 240. Electrical connector plug 220 may further comprise an elongate stiffening member 244 positioned in linear support structure 222. Elongate stiffening member 244 is configured to provide electrical connector plug 220 with rigidity, thereby permitting insertion and/or removal of electrical connector plug 220 into/from electrical connector receptacle 250 with a minimal amount of force. In embodiments of the present invention, stiffening member 244 comprises a surgical grade stainless steel or titanium member substantially extending the length of linear support structure 222. It should be appreciated that stiffening member 244 may comprise any suitable shape or material that provides electrical connector plug 220 with rigidity. Furthermore, it should be appreciated that in embodiments of the present invention, linear support structure 222 may comprise an at least partially rigid material capable of permitting the insertion and removal of electrical connector plug 220 into/from electrical connector receptacle 250 with a minimum amount of force without the need for stiffening member 244.

As illustrated in FIG. 2C, electrical connector plug 220 comprises one or more retention ridges 230. As discussed below, retention ridges 230 are configured to mate with corresponding structures in electrical connector receptacle 250 to retain electrical connector plug 220 in position with respect to electrical connector receptacle 250.

FIG. 2C is a more detailed partial perspective view of stimulator unit 202 of FIG. 2A. As noted above, in the illustrated embodiments, electrical connector receptacle 250 located in exterior layer 204. In the illustrated embodiment, electrical connector receptacle 250 comprises one or more receptacle contacts 254. As described in below, receptacle contacts 254 are configured to be electrically coupled to plug contacts 224 when electrical connector plug 220 is mated with electrical connector receptacle 250.

In the embodiment of FIG. 2C, electrical connector receptacle 250 comprises aperture 252, having an aperture opening 256. In the illustrated embodiment, aperture 252 has a substantially circular cross-section extending the elongate length of aperture 252. Although aperture 252 and support structure 222 have been discussed herein as having elongate linear shapes, it should be appreciated that other shapes are within the scope of the present invention. For example, in certain embodiments, support structure 222 and aperture 252 may each comprise substantially square shapes.

Electrical connector receptacle 250 is electrically coupled to stimulator unit 202 via an array 262 of contact wires 264 extending through exterior layer 204. In the illustrated embodiment, receptacle contacts 254 are each connected to one or more contact wires 264. Contact wires 264 extend from receptacle contacts 254 through bulkhead 260 to other components of stimulator unit 202. In certain embodiments, contact wires 264 are configured to relay signals, such as stimulation signals, from components of stimulator unit 202 to receptacle contacts 254. In other embodiments, contact wires 264 may be further configured to relay signals from receptacle contacts 254 to components of stimulator unit 202.

In the embodiment shown in FIG. 2C, two contact wires 246 are provided for each receptacle contact 254. It should be appreciated that in alternative embodiments, more or less contact wires 264 may be used. For example, in certain embodiments, three or more contact wires 264 may be provided for connection to each receptacle contact 254. In other embodiments, a single contact wire may be connected to one or more receptacle contacts 254.

As noted above, in the embodiment illustrated in FIG. 2C, contact wires 264 extend through bulkhead 260. Bulkhead 260 may be configured to provide structural support for contact wires 264, thereby increasing the durability of contact array 262. Bulkhead 260 may further comprise an insulating material so as to electrically isolate contact wires from one another.

In embodiments of the present invention, connections between two or more contacts wires 264 or between contacts wires 264 and receptacle contacts 254 may be provided by metal-to-metal welds. At the point where contacts wires 264 or contacts wires 264 and receptacle contacts 254 join, a metal-to-metal weld may be provided by establishing an electric current through the joining elements. Upon the application of electric current through the connecting members, the small mass of metal at the connection point will be caused to melt so as to form a continuous bridge there between.

To perform the contact welding process of two or more contacts wires 264 or contacts wires 264 and receptacle contacts 254, an induction coil (not shown) is associated with stimulator unit 202. The induction coil is energized by an external high frequency magnetic source. An array of capacitors is configured to distribute the applied signal induced in the coil through the contact wires 264 and/or receptacle contacts 254. In preferred embodiments of the present invention, the increased current may be provided during the manufacturing process or while stimulator unit 202 is implanted in the recipient. In such embodiments, although the applied current is sufficient to cause metal-to-metal weld, the recipient will not feel any sensation.

As illustrated in FIG. 2C, electrical connector receptacle 250 comprises one or more retention grooves 258. As discussed below, retention grooves 258 are configured to mate with retention ridges 230 of electrical connector plug 220.

FIG. 2D is a partial perspective view of stimulator unit 202 having electrical connector plug 220 mated with electrical connector receptacle 250. As shown in FIG. 2D, retention ridges 230 are illustrated mated with retention grooves 258. As noted above, in this mated configuration, retention ridges 230 and retention grooves 258 cooperate to releasable retain electrical connector plug 220 in position with respect to electrical connector receptacle 250. In embodiments of the present invention, electrical connector receptacle 250 and electrical connector plug 220 are configured such that the mating of retention ridges 230 with retention grooves 258 positions one or more plug contacts 224 to be electrically coupled to corresponding one or more receptacle contacts 254.

In the embodiment illustrated in FIG. 2D, receptacle contacts 254 and plug contacts 224 are electrically coupled by a physical connection between the contacts. However, it should be appreciated that receptacle contacts 254 and plug contacts 224 may be electrically coupled without a physical connection. For example, in certain embodiments, receptacle contacts 254 and plug contacts 224 may comprise capacitive plates that are configured to pass electrical signals without being physically connected to one another.

When electrical connector plug 220 is positioned in electrical connector receptacle 250 so that one or more plug contacts 224 are electrically coupled to corresponding one or more receptacle contacts 254, stimulator unit 202 and electrode assembly 240 become electrical connected. In the embodiments illustrated in FIG. 2D, signals may be transmitted from stimulator unit 202 to electrodes 238 via electrically coupled contacts 254 and 224 and leads 232. In further embodiments, an electrode 238 may transmit signals to stimulator unit 202 via contacts 254 and 224 and leads 232.

In the embodiment illustrated in FIG. 2D, retention ridges 230 of electrode connector plug 220 comprise two pairs of discrete convex structures positioned on opposite sides of linear support structure 222. Similarly, in the illustrated embodiment, retention grooves 258 comprise two pairs of discrete concave structures, each configured to receive one of the convex shaped retention ridges 230. Although the embodiment of FIG. 2B illustrates releasable locking arrangement 284 comprising two pairs of retention ridges 230, and retention grooves 258, it should be appreciated that locking arrangement 284 may comprise more or less pairs of retention ridges 230 and retention grooves 258. For example, in alternative embodiments, electrical connector plug 220 may comprise retention ridges 230 that substantially extend around the outside surface of linear support structure 222. In such embodiments, electrical connector receptacle 250 would comprise corresponding retention grooves 258. It should be appreciated that various combinations of the above embodiments are within the scope of the present invention.

In embodiments of the present invention, retention ridges 230 are configured to be mated with, and removed from, retention grooves 258 with a minimal amount of rotational and/or translational force. As such, retention ridges 230 may comprise a readily deformable material.

FIG. 2E is an enlarged view of the area of FIG. 2D bounded by a dashed circle and labeled as FIG. 2E. As described above, when electrical connector plug 220 is inserted into electrical connector receptacle 250, an electrical connection is created between stimulator unit 202 and electrodes 238. Also as noted above, in order to maintain the integrity of this electrical connection, a break-away sealing membrane 265 is provided. As shown in FIG. 2E, break-away sealing membrane 265 substantially prevents fluids from interfering with the electrical connection between plug contacts 224 and receptacle contacts 254.

As noted above, break-away sealing membrane 265 maintains the integrity of the electrical connection between electrical connector receptacle 250 and electrical connector plug 220. Break-away sealing membrane 265 is configured to be ruptured so as to allow stimulator unit 202 and electrode assembly 240 to be disconnected from each other with minimal force. In one embodiment, break-away sealing membrane 265 is configured to rupture when subjected to a force having a magnitude that is approximately the same as the magnitude of the force which is necessary to manually disconnect electrical connector plug 220 from electrical connector receptacle 250 without the presence of the break-away sealing membrane 265. In one specific embodiment, sealing membrane 265 is configured to rupture when subjected to a manual force applied by a surgeon to manually disconnect electrical connector plug 220 from electrical connector receptacle 250 from one another.

As noted above, one or both of the electrical connector halves may be directly attached to or integrated with their respective components. In certain applications of the present invention, one or both of electrode assembly 240 and stimulator unit 202 are electrically coupled to their respective connector halves, electrical connector plug 220 and electrical connector receptacle 250, via a flexible element or cable. Such a flexible element is configured to allow electrical connector plug 220 or electrical connector receptacle 250 to be moved within the patient adjacent to, or within the surgical space without causing movement of its associated component, electrode assembly 240 or stimulator unit 202, respectfully. This permits the physical separation of electrode assembly 240 and stimulator unit 202 without causing translation, rotation or otherwise physically disturbing one electrode assembly 240.

In the embodiments illustrated in FIG. 2E, break-away sealing membrane 265 is applied to the surface of exterior layer 204 circumferentially about electrical connector plug 220 at opening 256. As such, in this embodiment, break-away sealing membrane 265 substantially prevents the ingress of fluid through opening 256.

In certain embodiments, the rupture in break-away sealing membrane 265 may result from the manual application of a force, for example, via a medical instrument such as a scalpel. In other embodiments, break-away sealing membrane 265 may be ruptured by exerting a minimal rotational, translational, or other force on electrical cable 208 or electrical connector plug 220. In these embodiments, a surgeon may slightly twist, pull, or otherwise move electrical cable 208 or electrical connector plug 220 so as to cause break-away sealing membrane 265 to rupture. It should be appreciated that break-away sealing membrane 265 may be configured to rupture as a result of various other forces or mechanisms, and the above examples have merely been provided for illustration.

Although break-away sealing membrane 265 has been discussed thus far has a sealing element that is separate from exterior layer 204, it should be appreciated that in certain embodiments, break-away sealing membrane 265 may comprise a portion of exterior layer 204. In such embodiments, break-away sealing membrane 265 may comprise the same or similar materials as described above with reference to FIG. 2A, such as silicone, parylene, silicone elastomer, or any other biocompatible material that may be configured for sealing of the junction region. In certain embodiments, the sealing membrane may be configured to provide a hermetic seal.

In embodiments of the present invention in which break-away sealing membrane 265 comprises a portion of exterior layer 204, break-away sealing membrane 265 comprises a portion of exterior layer 204 having a thickness that is substantially less than the remainder of exterior layer 204. In other embodiments of the present invention, exterior layer 204 may comprise first and second materials, each material having different rupture strengths. As used herein, rupture strength refers to the ability of a material to withstand the application of a force before rupturing. A difference in rupture strength may also be provided by using different grades of a material. In such embodiments in which exterior layer 204 comprises different grades or different materials, the first material having greater rupture strength is configured to substantially cover stimulator unit 202, while break-away membrane 265 comprises the second material having lower rupture strength. As such, in these embodiments, the first material is configured to remain intact upon the application of a force to break-away sealing membrane 265.

In still other embodiments of the present invention, break-away sealing membrane 265 may comprise portion of exterior layer 204 that is substantially surrounded by, or is adjacent to, a mechanical weakness. In such embodiments, the application of a minimal force to break-away sealing membrane 265 results in a rupture occurring at the mechanical weakness. In these embodiments, the mechanical weakness in exterior layer 204 may comprise a score, notch, or any other intentionally created weakness that permits ready rupturing, yet is capable of maintaining the integrity of the seal prior to application of the minimal force.

It should be further appreciated that in alternative embodiments of the present invention, the mechanical weakness discussed above may be provided in embodiments in which break-away sealing membrane 265 comprises a sealing element that is separate from exterior layer 204. As would be appreciated, in such embodiments, break-away sealing membrane 265 would be configured to rupture at the mechanical weakness, In further embodiments of the present invention, exterior layer 204 may include a rupture limiting arrangement configured to limit a rupture, and to prevent any rupture in break-away sealing membrane 265 from spreading to the remainder of exterior layer 204. In such embodiments, the rupture limiting arrangement may comprise one or more implanted members adjacent to, or substantially surrounding, break-away sealing membrane 265. For example, such a rupture limiting mechanism may be provided by including metal members within outer coating 204. In such embodiments, the metal members may be configured to act as internal cutting members upon the application of a force to break-away sealing membrane 265. In a specific embodiment of the present invention, a pair of adjacent yet physically spaced metal members, each having a sharp portion, is disposed in exterior layer 204. In such specific embodiments, if a force were applied, the sharp portions of the spaced members would result in a rupture occurring substantially between the metal members. In other embodiments, the rupture limiting arrangement may comprise an additional mechanical weakness adjacent to, or substantially surrounding, break-away sealing membrane 265.

In the embodiments illustrated in FIGS. 2A-2E, electrical connector receptacle 250 is located in exterior layer 204, and break-away sealing membrane 265 is integrated with, or positioned on, the surface of exterior layer 204 circumferentially around electrical connector plug 220 at opening 256. However, as noted above, in alternative embodiments of the present invention, electrical connector receptacle 250 is not necessarily located in exterior layer 204.

In one such alternative embodiment, electrical connector receptacle 250 and stimulator unit 202 may be located in physically separate housings. In other embodiments, electrical connector receptacle 250 may comprise a stand-alone component. In both of these embodiments, electrical connector receptacle 250 may be connected to stimulator unit via a flexible element, such as a flexible electrical cable described above with reference to FIG. 2A, or via a hardwire connection. Similarly, in both of these embodiments, break-away sealing membrane 265 is provided to maintain the integrity of the connection between electrical connector receptacle 250 and electrical connector plug 220.

In embodiments of the present invention illustrated in FIG. 3, electrical connector receptacle 250 and electrical connector plug 220 are configured to provide a minimum leakage volume there between. In these embodiments, electrical connector receptacle 250 and electrical connector plug 220 are designed such that if a fluid penetrates break-away sealing membrane 265, the space between the connector halves is sufficiently small that the fluid will not interfere with the electrical connection between electrical contacts 224, 254. In certain embodiments, at least one of electrical connector receptacle 250 and electrical connector plug 220 comprises a gap consuming compliant material configured to substantially fill any space between electrical connector receptacle 250 and electrical connector plug 220, thereby providing the minimum leakage volume.

As noted above with reference to FIG. 2A, in embodiments of the present invention, electrical cable 208 electrically couples electrical connector plug 220 to electrode assembly 240 to assist in disconnection of electrical connector plug 220 and electrical connector receptacle 250 without disturbing implanted electrode assembly 240. However, as noted above, in alternative embodiments, an electrical connector receptacle 250 is coupled to stimulator unit 202 via a flexible element, such as a flexible cable. In such embodiments, the flexible cable coupling electrical connector receptacle 250 assists in the physical separation of stimulator unit 202 from electrode assembly 240 without causing translation, rotation or otherwise physically disturbing electrode assembly 240 implanted in the cochlea of the recipient. In such embodiments, following the rupture of break-away sealing membrane 265, electrical connector plug 250 and thus stimulator unit 202 may be moved or repositioned with disturbing the position of electrode assembly 240. In still other embodiments, flexible cables are used to couple electrical connector plug 220 and electrical connector receptacle 250 to electrode assembly 240 and stimulator unit 202 respectively.

FIG. 3 is a flowchart illustrating the manufacturing of an electrically connected stimulator unit and electrode assembly of a cochlear implant in accordance with embodiments of the present invention. FIG. 3 includes blocks 302, 304, 306, 308 and 310. At block 302 the manufacturing process begins. At block 304 a stimulator unit that is electrically coupled to a first connector half is provided. In embodiments of the present invention, the stimulator unit may be a pre-manufactured component. In other embodiments, the stimulator unit may be provided by assembling one or more components.

At block 306, a second connector half electrically coupled to an electrode assembly is mated with the first half of electrical connector electrically coupled to the stimulator unit. Upon the mating of the two connector halves, an electrical connection is provided between the stimulator unit and the electrode assembly. After mating of the connector halves, a break-away sealing membrane is provided to seal the electrical connection between the two connector halves at block 308. As explained above with reference to claim 1, the break-away sealing membrane may be applied via a coating process. Following the application of the break-away membrane, the manufacturing process ends at block 310.

FIG. 4 is a flowchart illustrating the replacement/adjustment of an implanted stimulator electrically connected to an electrode assembly implanted in a recipient in accordance with embodiments of the present invention. At block 452 the operation begins by opening the site of the implanted components. At block 454, the surgeon causes a slight amount of force to be applied to the break-away sealing membrane thereby rupturing the sealing membrane. Following rupture of the break-away sealing membrane, the first and second connector halves may be easily physically separated from each other. As noted above, in certain embodiments, the second connector half is electrically coupled to electrode assembly via a flexible electrical cable. In such embodiments, once the first and second connector halves have been physically separated, flexible electrical cable prevents movement of the first or second connector halves from being relayed to the electrode assembly implanted within the cochlear. As such, at block 456 the stimulator unit may be explanted from the recipient without physically disturbing the implanted electrode assembly.

At block 458, the explanted stimulator unit, or a replacement stimulator unit is implanted in the recipient. In embodiments in which a replacement stimulator unit is to be implanted, the replacement stimulator unit would be electrically coupled to a first connector half configured to mate with the second connector half coupled to the implanted electrode assembly. At block 460, the newly implanted stimulator unit is electrically connected to the electrode assembly by mating the first and second connector halves. Following connection of the two halves of the electrical connector plug, the rupture in the break-away sealing membrane may be resealed at block 462.

Various processes may be used to reseal the rupture in the break-away sealing membrane. For example, in certain embodiments, a partially set sealing material may be manually applied, to seal the rupture. In other embodiments, a fast drying sealing material may be brushed or sprayed onto the break-away sealing membrane to reseal the rupture. In further embodiments, a manually applied epoxy or other surface sealant may be used to reseal the rupture. In still other embodiments, a pre-set material overlay may be affixed over the rupture via a biocompatible adhesive, thereby sealing the rupture. In such embodiments, the overlay may be a pre-configured element or may be cut or trimmed to size by the surgeon.

Although FIG. 4 has been discussed in reference to resealing the rupture in the break-away sealing membrane, it should be appreciated that in other embodiments, a new break-away sealing membrane may be provided using the same or similar processes described above with reference to FIGS. 2A and 4.

Figure 5A:
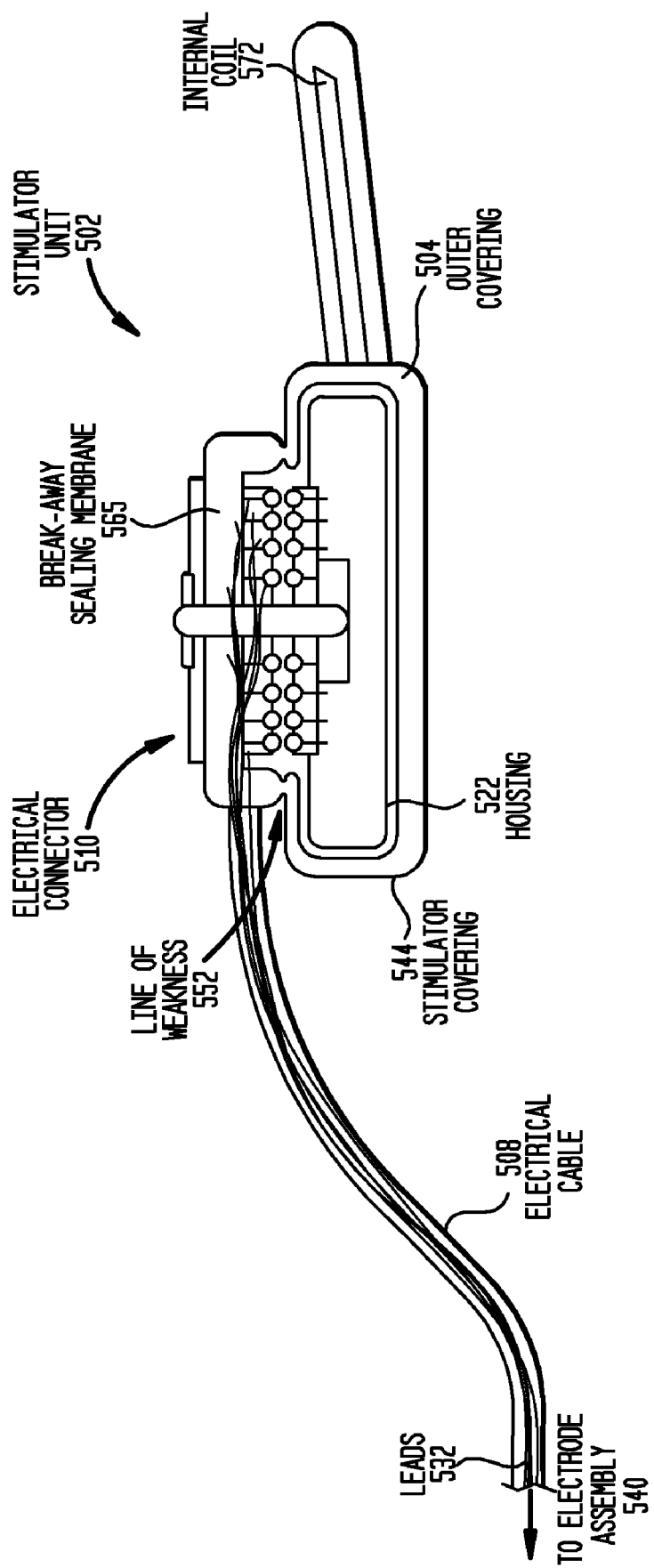
FIG. 5A is perspective view of an alternative embodiment of the stimulator unit depicted in FIG. 1 partially broken away to illustrate the electrical connection of the stimulator unit and the electrode assembly of FIG. 1 via an embodiment of the electrical connector of the present invention.

FIG. 5A illustrates a perspective view of alternative embodiments of an electrical connector of the present invention. Illustrated in FIG. 5A is an embodiment of stimulator unit 134, referred to as stimulator unit 502. Stimulator unit 502 comprises a housing 522 having therein similar or same components as stimulator unit 134 of FIG. 1. In the illustrated embodiments, housing 522 is sealed by a biocompatible exterior layer 504 that is substantially similar exterior layer 204 of FIGS. 2A-2E. Connected to stimulator unit 502 is internal coil 572 which is similar to internal coil 132 of FIG. 1. In the embodiments of FIG. 5A, an electrode assembly 540 (not shown) is electrically connected to stimulator unit 502 via an electrical connector 510. Details of electrical connector 510 are described below with reference to FIG. 5B.

Figure 5B:
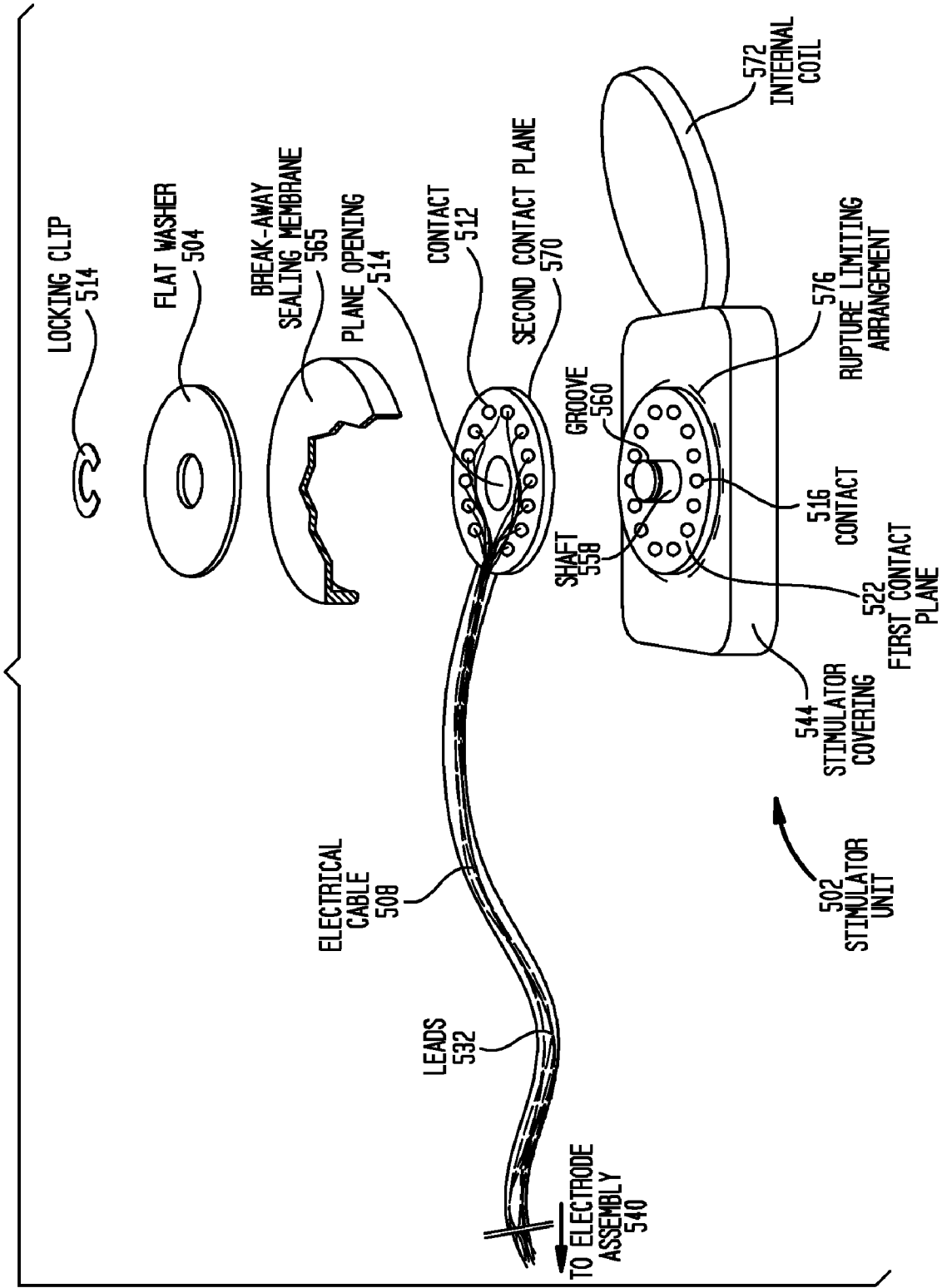
FIG. 5B is an exploded view of the electrical connector illustrated in FIG. 5A.

FIG. 5B illustrates an exploded view of an electrical connector 510 configured to electrically connect electrode assembly 540 with stimulator unit 502. In the embodiment illustrated in FIG. 5B, electrical connector 510 comprises two connector halves. A first connector half of electrical connector 510 is electrically coupled to stimulator unit 502 and comprises a first contact plane 522 having one or more contacts 516 positioned therein or thereon. In the embodiment illustrated in FIG. 5B, first contact plane 522 may comprise a feedthrough insulator configured to electrically isolate contacts 516 from one another. As discussed below in more detail, first contact 552 further includes an elongate shaft 558 distally extending there from. Shaft 558 has disposed thereon a groove 560. Shaft 558 and groove 560 are described below.

In the embodiment illustrated in FIG. 5B, contacts 516 may be connected to one or more contact wires (not shown) extending from contacts 516 to other components of stimulator unit 502. In certain embodiments, the contact wires are configured to relay signals, such as stimulation signals, from the components of stimulator unit 502 to contacts 516. In other embodiments, the contact wires may be further configured to relay signals from contacts 516 to other components of stimulator unit 502. It should be appreciated that any number of the contact wires may be used. For example, in certain embodiments, two or more contact wires may be provided for connection to each contact 516. In other embodiments, a single contact wire may be connected to one or more contacts 516.

In the illustrated embodiment, the second connector half of electrical connector 510 comprises a second contact plane 570 electrically coupled to electrode assembly 540. Second contact plane 570 includes one or more contacts 512 positioned therein or thereon. As described below, contacts 512 are configured to be electrically coupled to contacts 516 of first contact plane 552. As described below, second contact plane 570 comprises an opening, referred to as plane opening 514, extending there through.

Connected to one or more contacts 512 are one or more leads 532. Leads 532 extend from contacts 512 through an electrical cable 508 to one or more electrodes of electrode assembly 540. In embodiments of FIG. 5B, a single lead 532 extends between a single plug contact 512 and a corresponding electrode. However, it should be appreciated that in alternative embodiments of the present invention, a lead 532 may extend between any number of contacts 512 or electrodes. For example, a lead 532 may extend from one contact 512 to a plurality of electrodes. Likewise, in alternative embodiments, a lead 532 may extend from a plurality of contacts 512 to a single electrode.

As noted, leads 532 extend to electrode assembly 540 through electrical cable 508. In these embodiments, electrical cable 508 comprises a flexible cable having one or more lumens there through. Leads 532 extend through these lumens.

As noted above, in the embodiments illustrated in FIG. 5B, first and second planes 522, 570 are configured to mate with each other to electrically connect stimulator unit 502 and electrode assembly 540. The mating of first and second contact planes 552, 570 refers to the positioning of the contact planes coaxially adjacent one another so that an electrical connection may be formed between one or more contacts 516 and one or more contacts 512. More specifically, in the illustrated embodiment, first and second planes 522, 570 are mated with one another by placing plane opening 514 over shaft 558, and sliding second plane 570 over shaft 558 until second contact plane 570 is coaxially adjacent first contact plane 522.

Once first and second contact planes 552, 570 are positioned coaxially adjacent one another, contacts planes 522 and 570 may be rotated with respect to one another so that contacts 516 positioned of first contact plane 522 may be electrically coupled to contacts 512 of second plane 570.

When contacts planes 522 and 570 are mated with one another, electrical connector 510 is sealed to maintain the integrity of the electrical connection between contact planes 522, 570. The seal is provided by a break-away sealing membrane 565 that protects at least the electrical connections between contact planes 522, 570. Break-away sealing membrane 565 is configured to be ruptured so as to allow stimulator unit 502 and electrode assembly 540 to be disconnected from each other with minimal force. In one embodiment, break-away sealing membrane 565 is configured to rupture when subjected to a force having a magnitude that is approximately the same as the magnitude of the force which is necessary to manually disconnect contact plane 570 from contact plane 522 without the presence of the break-away sealing membrane 565. In one specific embodiment, sealing membrane 565 is configured to rupture when subjected to a manual force applied by a surgeon to manually disconnect contact plane 570 from contact plane 522.

In certain applications of the present invention, one or both of electrode assembly 540 and stimulator unit 502 are electrically coupled to their respective contact planes 570, 522 via a flexible element or cable. Such a flexible element is configured to allow a contact plane 570, 522 to be moved within the patient adjacent to, or within, the surgical space without causing movement of its associated component, electrode assembly 540 or stimulator unit 502, respectfully. This permits the physical separation of electrode assembly 540 and stimulator unit 502 without causing translation, rotation or otherwise physically disturbing electrode assembly 540. In some embodiments, the ability to disconnect stimulator unit 502 without disturbing electrode assembly 540 permits the independent explantation of stimulator unit 502 from the recipient while leaving electrode assembly 540 implanted in the cochlea of the recipient. In such embodiments, subsequent connection of a repaired or replacement stimulator unit 502 may be attained by mating contact plane 570 with contact plane 522 and reestablishing break-away sealing membrane 565.

Break-away sealing membrane 565 may be similar to break-away sealing membrane 265 of FIGS. 2A-2E in that break-away sealing membrane 565 may also comprise silicone, parylene, silicone elastomer, or any other biocompatible material that may be configured for sealing the electrical connection between first and second planes 522, 570. In the illustrated embodiment, break-away sealing membrane 565 provides a layer of sealing material surrounding coaxially adjacent contact planes 522, 570 to substantially prevent the ingress of fluid to the electrical connection between contacts 516, 512. Moreover, in certain embodiments of the present invention, flexible cable 508, is provided to electrically couple second contact plane 570 to electrode assembly 540. In these embodiments, flexible cable 508 assists in the physical separation of stimulator unit 502 from electrode assembly 540 without causing translation, rotation or otherwise physically disturbing electrode assembly 540 implanted in the cochlea of the recipient.

In certain embodiments, the rupture in break-away sealing membrane 565 may result from the manual application of a force, for example, via a medical instrument such as a scalpel. In other embodiments, break-away sealing membrane 565 may be ruptured by exerting a minimal rotational, translational, or other force on electrical cable 508 or second contact plane 570. In these embodiments, a surgeon may slightly twist, pull, or otherwise move electrical cable 508 or second contact plane 570 so as to cause break-away sealing membrane 565 to rupture. It should be appreciated that break-away sealing membrane 265 may be configured to rupture as a result of various other forces or mechanisms, and the above examples have merely been provided for illustration.

In embodiments of the present invention illustrated in FIG. 5B, contacts planes 522 and 570 are configured to provide a minimum leakage volume there between. In these embodiments, electrical contacts planes 522 and 570 are designed such that if a fluid penetrates break-away sealing membrane 265, the space between the connector halves is sufficiently small that the fluid will not interfere with the electrical connection there between. In certain embodiments, at least one of contacts planes 522 and 570 comprises a gap consuming compliant material configured to substantially fill any space there between, thereby providing the minimum leakage volume.

In embodiments of the present invention, break-away sealing membrane 565 may comprise a portion of exterior layer 504. In certain embodiments, similar to embodiments of break-away sealing membrane 265 discussed above, break-away sealing membrane 565 may comprise a portion of exterior layer 504 having a thickness that is substantially less than the remainder of exterior layer 504. Also similar to embodiments discussed above with reference to break-away sealing membrane 265, exterior layer 504 may comprise first and second materials, each material having different rupture strengths, and break-away sealing membrane may comprise a portion of exterior layer 504 having lower rupture strength.

In embodiments illustrated in FIGS. 5A-5B, break-away sealing membrane 565 may have integrated therein, or be adjacent to, a mechanical weakness, illustrated in FIG. 5A as line of weakness 552. In such embodiments, break-away sealing membrane 565 may be configured to rupture at line of weakness 552. FIG. 5A illustrates such an embodiment having a mechanical weakness at the area in which break-away sealing membrane 565 is connects to stimulator covering 544. As described above with reference to FIG. 2A, the mechanical weakness may comprise a score, notch, or other intentionally created weakness.

In further embodiments of the present invention, exterior layer 504 may include a rupture limiting arrangement 576 configured to prevent any rupture in break-away sealing membrane 565 from spreading to stimulator covering 544. As shown in FIG. 5B, rupture limiting arrangement 576 may be provided by including metal members within stimulator covering 544. In such embodiments, the metal members may be configured to act as internal cutting members upon the application of a force to break-away sealing membrane 565. In a specific embodiment of the present invention, the metal members comprise a pair of adjacent yet physically spaced metal members each having a sharp portion. In such specific embodiments, if a force were applied, the sharp portions of the spaced members would result in a rupture occurring substantially between the metal members. In other embodiments, rupture limiting arrangement 576 may comprise an additional mechanical weakness.

In certain embodiments, break-away sealing membrane 565 may be configured to have sufficient strength to retain first and second contact planes 522, 570 in position with respect to each other. In other embodiments, plane opening 514 may be configured to frictionally engage shaft 558 to prevent movement of second contact plane 570 with respect to first contact plane 522.

In still other embodiments, a locking arrangement may be provided to retain second contact plane 570 in position with respect to first contact plane 522. In such embodiments of the present invention, a locking arrangement in the form of locking clip 514 may be provided. As noted above, shaft 558 comprises a groove 560 therein. Locking clip 514 may be configured to engage groove 560 to exert a force on contact 510. In such an embodiment, the force on second contact plane 570 would substantially prevent second contact plane 570 from moving with respect to first contact plane 522. In specific embodiments of the present invention, a washer 504 may be further provided to spread the pressure from locking clip 514.

In the illustrated embodiment, first and second contact planes 522, 570 each have a substantially cylindrical shape. However, it should be appreciated that in alternative embodiments of the present invention first and second contact planes 522, 570 may have other shapes, such as a square shape, rectangular shape, etc.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. A medical device comprising:
   first and second implantable components;
   an electrical connector configured to electrically connect said first and second components, comprising:
      first and second connector halves electrically connected to one another and electrically coupled to said first and second components, respectively, and
      a sealing membrane configured to seal the electrical connection between said first and second connector halves, wherein said sealing membrane is configured to be ruptured with a minimal amount of force in order to separate said first and second connector halves from each other.

2. The device of claim 1, wherein when said first and second connector halves are electrically connected, said connector halves are configured to provide a minimum leakage volume therebetween.

3. The device of claim 2, wherein at least one of said first and second connector halves further comprises a gap consuming compliant material configured to substantially fill any space between said connector halves.

4. The device of claim 1, wherein said sealing membrane comprises a barrier configured to substantially prevent the ingress of fluid through said barrier.

5. The device of claim 1, wherein at least one of said connector halves is electrically coupled to either said first or second implantable component, respectively, via a flexible electrical cable.

6. The device of claim 1, wherein said first connector half comprises an electrical connector plug, and wherein said second connector half comprises an electrical connector receptacle having an opening configured to receive said electrical connector plug.

7. The device of claim 6, wherein when said plug is inserted into said receptacle, said sealing membrane is at least disposed around said plug so as to seal said opening of said receptacle.

8. The device of claim 6, further comprising:
   a releasable locking arrangement configured to retain said plug in position with respect to said receptacle so as to ensure that said first and second implantable components remain electrically connected.

9. The device of claim 8, wherein said electrical connector plug comprises one or more retention ridges, and wherein said electrical connector receptacle comprises one or more retention grooves configured to receive and couple with said one or more retention ridges, and wherein said locking arrangement comprises said ridges and said grooves.

10. The device of claim 9, wherein said retention ridges comprise a readily deformable material, and wherein said retention ridges are configured to be decoupled from said retention grooves with a minimal amount of force.

11. The device of claim 1, wherein said first and second connector halves comprise first and second electrical contact planes, respectively, configured to be positioned co-axially adjacent one another to create said electrical connection.

12. The device of claim 11, wherein said second contact plane comprises a circumferential disk having an opening therethrough, and wherein said first contact plane comprises a circumferential disk having a shaft extending therefrom, and wherein said opening is configured to receive said shaft so that said first and second contact planes are co-axially adjacent one another.

13. The device of claim 12, wherein said shaft has a groove therein, and wherein when said contact planes are co-axially adjacent, said groove is configured to mate with a clip apparatus to retain said contact planes in position with respect to one another.

14. The device of claim 1, further comprising:
an exterior layer applied to said first component and configured seal said first component.

15. The device of claim 14, wherein said sealing membrane comprises a portion of said exterior layer.

16. The device of claim 15, wherein said sealing membrane comprises a portion of said exterior layer having a thickness that is substantially less than the remainder of said exterior layer.

17. The device of claim 14, wherein said exterior layer comprises first and second materials, said second material having a rupture strength that is less than said first material, and wherein said first material substantially covers said first component and wherein said sealing membrane comprises said second material.

18. The device of claim 15, wherein said sealing membrane comprises a portion of said exterior layer substantially surrounded by a mechanical weakness such that said sealing membrane is configured to rupture at said mechanical weakness.

19. The device of claim 15, wherein said exterior layer includes a rupture limiting arrangement configured to prevent said rupture in said sealing membrane from spreading to the remainder of said exterior layer.

20. The device of claim 1, wherein said first implantable component comprises a stimulator unit, and wherein said second implantable component comprises an electrode assembly.

21. A method of reconfiguring a first implanted component electrically connected to a second implanted component via an electrical connector, said electrical connector comprising first and second connector halves electrically coupled to said first and second components, respectively, and a sealing membrane configured to seal the sealing the electrical connection between said first and second connector halves, said method comprising:
opening the site of said implanted components;
rupturing said sealing membrane with the application of minimal force;
separating said connector halves so as to electrically disconnect said first and second components; and
adjusting the configuration of said first component.

22. The method of claim 21, wherein adjusting the configuration of said first component comprises:
explanting said first component;
implanting a third component, said third component electrically coupled to a half of an electrical connector configured to mate with said second connector half;
electrically connecting said connector half coupled to said third component with said connector half coupled to said second component; and
sealing the electrical connection between said connector halves.

23. The method of claim 21, wherein adjusting the configuration of said first component comprises:
explanting said first component;
modifying said first component;
reimplanting said first component;
electrically connecting said connector half coupled to said first component with said connector half coupled to said second component; and
sealing the electrical connection between said connector halves.

24. The method of claim 21, wherein when said first and second connector halves are electrically connected, said connector halves are configured to provide a minimum leakage volume therebetween.

25. The method of claim 24, wherein at least one of said first and second connector halves further comprises a gap consuming compliant material configured to substantially fill any space between said connector halves.

26. The method of claim 21, wherein said sealing membrane comprises a barrier configured to substantially prevent the ingress of fluid therethrough.

27. The method of claim 21, wherein at least one of said connector halves is electrically coupled to either said first or second implantable component, respectively, via a flexible electrical cable.

28. A method of manufacturing a medical device, comprising:
providing a first implantable component electrically coupled to a first connector half;
providing a second implantable component electrically coupled to a second connector half;
physically and electrically connecting said first and second connector halves so as to electrically connect said first and second components; and
sealing the electrical connection between said first and second halves with a sealing membrane, wherein said sealing membrane is configured to be ruptured upon the application of a minimal force in order to separate said first and second connector halves from each other.

29. The method of claim 28, wherein sealing the electrical connection comprises:
sealing said connection with a barrier configured to substantially prevent the ingress of fluid therethrough.

30. The method of claim 29, wherein sealing said connection with said barrier comprises:
coating said electrical connection with a biocompatible silicone elastomer material.

31. The device of claim 28, wherein when said first and second connector halves are electrically connected, said connector halves are configured to provide a minimum leakage volume therebetween.

32. The device of claim 31, wherein at least one of said first and second connector halves further comprises a gap consuming compliant material configured to substantially fill any space between said connector halves.

33. The method of claim 28, wherein at least one of said connector halves is electrically coupled to either said first or second implantable component, respectively, via a flexible electrical cable.

34. The method of claim 28, wherein said first connector half comprises an electrical connector plug, and wherein said second connector half comprises an electrical connector receptacle having an opening to receive said electrical connector plug, and wherein physically and electrically connecting said first and second connector halves comprises:
inserting said electrical connector plug into said electrical connector receptacle.

35. The method of claim 34, wherein sealing the electrical connection between said first and second halves comprises:
applying said sealing membrane around said plug so as to seal said opening of said receptacle.

36. The method of claim 28, wherein said first and second connector halves comprise first and second electrical contact planes, respectively, configured to be positioned co-axially adjacent one another to create said electrical connection.

37. The method of claim 36, wherein said second contact plane comprises a circumferential disk having an opening therethrough, and wherein said first contact plane comprises a circumferential disk having a shaft extending therefrom, and wherein physically and electrically connectin said first and second connector halves comprises:
positioning said opening over said shaft so that said first and second contact planes are co-axially adjacent one another.

38. A connector for electrical connecting first and second implantable components comprising:
first and second connector halves electrically connected to one another and electrically coupled to said first and second components, respectively, and
a sealing membrane configured to seal the electrical connection between said first and second connector halves, wherein said sealing membrane is configured to be ruptured with a minimal amount of force in order to separate said first and second connector halves may be readily disconnected from each other.

39. The device of claim 38, wherein when said first and second connector halves are electrically connected, said connector halves are configured to provide a minimum leakage volume therebetween.

40. The device of claim 39, wherein at least one of said first and second connector halves further comprises a gap consuming compliant material configured to substantially fill any space between said connector halves.

41. The device of claim 38, wherein said sealing membrane comprises a barrier configured to substantially prevent the ingress of fluid therethrough.

42. The connector of claim 38, wherein at least one of said connector halves is electrically coupled to either said first or second implantable component, respectively, via a flexible electrical cable.

43. The connector of claim 38, wherein said first connector half comprises an electrical connector plug, and wherein said second connector half comprises an electrical connector receptacle.

44. The connector of claim 38, wherein said first and second connector halves comprise first and second electrical contact planes, respectively, configured to be positioned co-axially adjacent one another to create said electrical connection.

45. The device of claim 44, wherein said second contact plane comprises a circumferential disk having an opening therethrough, and wherein said first contact plane comprises a circumferential disk having a shaft extending therefrom, and wherein said opening is configured to receive said shaft so that said first and second contact planes are co-axially adjacent one another.

46. The device of claim 1, wherein the seal is a hermetic seal.

47. The method of claim 21, wherein the seal is a hermetic seal.

48. The method of claim 28, wherein the seal is a hermetic seal.

49. The connector of claim 38, wherein the seal is a hermetic seal.

\* \* \* \* \*